(12) United States Patent
Volkin et al.

(10) Patent No.: US 6,245,568 B1
(45) Date of Patent: Jun. 12, 2001

(54) HUMAN PAPILLOMA VIRUS VACCINE WITH DISASSEMBLED AND REASSEMBLED VIRUS-LIKE PARTICLES

(75) Inventors: David B. Volkin, Doylestown; Henryk Mach, Ambler; Li Shi, Eagleville, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/524,624

(22) Filed: Mar. 13, 2000

Related U.S. Application Data

(60) Provisional application No. 60/126,528, filed on Mar. 26, 1999.

(51) Int. Cl.[7] ............................. G01N 31/00; A61K 39/12
(52) U.S. Cl. ............................. 436/8; 430/18; 424/204.1; 530/300; 530/350
(58) Field of Search ....................... 436/8, 18; 424/204.1; 530/350, 300

(56) References Cited

FOREIGN PATENT DOCUMENTS

WO 98/44944   10/1998   (WO).
WO 99/01557   1/1999   (WO).

OTHER PUBLICATIONS

Brady, et al., J. Virology vol. 23 (3): 1977, pp. 717–724.
Saluuke, et al., Biophysical Journal 56: 1989, pp. 887–900.
Li, et al., J. Virology, 71 (4): 1997 pp. 2988–2995.
McCarthy, et al., J. Virology 72(1): 1998 pp. 32–41.
Zhang, et al., Virology 243: 1998 pp. 423–431.
Rose, et al., J. Virology 67(4): 1993 pp. 1936–1944.
Hsu, Virology 69: 1976, pp. 587–595.
Garcea, et al., Nature 329: 1987 pp. 86–87.
Saluuke et al., Cell 46: 1986 pp. 895–904.
Montross, et al., J. Virology 65: 1991 pp. 4991–4998.
Kirnbauer, et al., PNAS 89: 1992 pp. 12180–12184.
Itagensee J. Virology 67: 1993 pp. 315–322.
Kirnbauer J. Virology 67: 1993 pp. 6929–6936.
Zhou J. Gen Virology 74: 1993 pp. 763–768.
Sapp J. Gen Virology 76: 1995 pp. 2407–2412.
Belnap J. Mol. Biol. 259: 1996 pp. 249–263.
Li J. Virology 72: 1998 pp. 2160–2167.
Sapp J. Virology 72: 1998 pp. 6186–6189.
Kawana J. Virology 72: 1998 pp. 10298–10300.
Search Report for PCT counterpart of this application.

Primary Examiner—Ali R. Salimi
(74) Attorney, Agent, or Firm—Joanne M. Giesser; Jack L. Tribble

(57) ABSTRACT

Human Papillomavirus vaccine formulations which contain virus-like particles (VLPs) can be made more stable and have an enhanced shelf-life, by treating the VLPs to a disassembly and reassembly process. Also provided are formulation buffers to long term stable storage of VLPs.

17 Claims, 14 Drawing Sheets

HUMAN PAPILLOMA VIRUS VACCINE WITH DISASSEMBLED AND REASSEMBLED VIRUS-LIKE PARTICLES

This application claims priority from U.S. Provisional Patent Application No. 60/126,528, filed Mar. 26, 1999.

BRIEF DESCRIPTION OF THE INVENTION

This invention relates to a human papillomavirus (HPV) vaccine which contains virus-like particles (VLPs) which have been disassembled into capsomeres and then reassembled into VLPs. This invention also relates to processes of making this vaccine resulting in more homogeneous HPV VLPs and greatly improved storage stability.

BACKGROUND OF THE INVENTION

Human Papillomavirus (HPV) infects the genital tract and has been associated with various dysplasias, cancers, and other diseases. These diseases are currently targets for vaccine development and vaccines containing virus-like particles (VLPs) which contain L1 or the combination of L1+L2 proteins are currently in clinical trials.

It has been found, however, that recombinant L1 protein HPV VLPs purified from yeast are not stable during long-term storage, either in solution or when adsorbed onto aluminum adjuvant particles.

In the past, various researchers have investigated the conditions of HPV VLP assembly and disassembly. For example, McCarthy et al, 1998 "Quantitative Disassembly and Reassembly of Human Papillomavirus Type 11 Virus-like Particles in Vitro" *J. Virology* 72(1):32–41, describes the disassembly and reassembly of recombinant L1 HPV 11 VLPs purified from insect cells in order to obtain a homogeneous preparation of VLPs. A prolonged incubation (about 16 hours at 4° C.) with a relatively high concentration of reducing agent at physiological ionic strength was used to disassemble the VLPs, and removal of the reducing agent at a higher ionic strength was used to reassemble the VLPs. This method is quite time-consuming, however.

In order to develop a commercially useful vaccine, a storage stable formulation is needed. It would be desirable to have a relatively simple, quick and quantitative treatment procedure for making a storage stable HPV VLP formulation.

DETAILED DESCRIPTION OF THE INVENTION

This invention relates to a process for making stable human papillomavirus (HPV) virus-like particles (VLPs), the process comprising the steps of:
 (a) incubating VLPs in a dissociation mixture comprising a relatively low concentration of a reducing agent, a salt present in a range from physiological ionic strength up to 1.25M, a non-ionic surfactant, a metal chelating agent and a buffer until disassembled VLPs are produced;
 (b) removing the reducing agent from the dissociation mixture; and
 (c) reassembling the disassembled VLPs into VLPs.

In some embodiments, the reassembled VLPs are adsorbed onto an aluminum adjuvant.

This invention also relates to VLPs made by a process comprising the steps of:
 (a) incubating purified VLPs in a high salt dissociation mixture comprising a relatively low concentration of a reducing agent, a salt present in a range of 0.5 M to 1.25M salt, a non-ionic surfactant, a metal chelating agent, and a buffer until disassembled VLPs are produced;
 (b) removing the reducing agent from the dissociation mixture; and
 (c) reassembling the disassembled VLPs; and
 (d) optionally adsorbing the reassembled HPV VLPs to aluminum adjuvant.

Another embodiment of this invention relates to VLPs made by a process comprising the steps of:
 (a) incubating purified VLPs in a low salt dissociation mixture comprising a relatively low concentration of a reducing agent, a salt present at approximately physiological ionic strength, a non-ionic surfactant, a metal chelating agent, and a buffer until disassembled VLPs are produced;
 (b) removing the reducing agent from the dissociation mixture; and
 (c) reassembling the disassembled VLPs; and
 (d) optionally adsorbing the reassembled HPV VLPs to aluminum adjuvant.

Another aspect of this invention relates to vaccines made from the VLPs produced by any of the above processes.

This invention also relates to vaccine formulations comprising VLPs made by the above processes, and which are stored in a formulation buffer. The formulation buffer comprises a salt, a histidine buffer, and a nonionic surfactant.

BRIEF DESCRIPTION OF THE FIGURES

FIG. 6A is HPV 6A; FIG. 6B is HPV 11; FIG. 6C is HPV 16; and FIG. 6D is HPV 18.

FIGS. 7A and 7B are HPV 6A; FIGS. 7C and 7D are HPV 11; FIGS. 7E and 7F are HPV 16; and FIGS. 7G and 7H are HPV 18 VLPs.

FIGS. 8A–F are comparisons of thermal stability and hydrodynamic size distribution of disassembled/ reassembled HPV 6a, HPV 11 and HPV 16 VLPs, prepared from a disassembly process either near physiological conditions (low salt process) or at higher salt concentrations (high salt process). These physical properties of the HPV VLPs were determined by cloud point analysis and analytical ultracentrifugation analysis. In the low salt process, HPV VLPs are disassembled in 0.166M NaCl, 10 mM TRIS solution (pH 8.2) while in the high salt process, HPV VLPs are disassembled in 0.63M NaCl, 35 mM Phosphate, and 100 mM TRIS solution (pH 8.2). Both solutions also contain EDTA and polysorbate 80. FIGS. 8A and 8B show the cloud point and analytical ultracentrifugation data of HPV 6A VLPs; FIGS. 8C and 8D show the same analysis with HPV 11 VLPs; FIGS. 8E and 8F show the same analysis with HPV 16 VLPs.

FIG. 9A is HPV 6a; FIG. 9B is HPV 1, FIG. 9C is HPV 16; and FIG. 9D is HPV 18.

Figure 1:
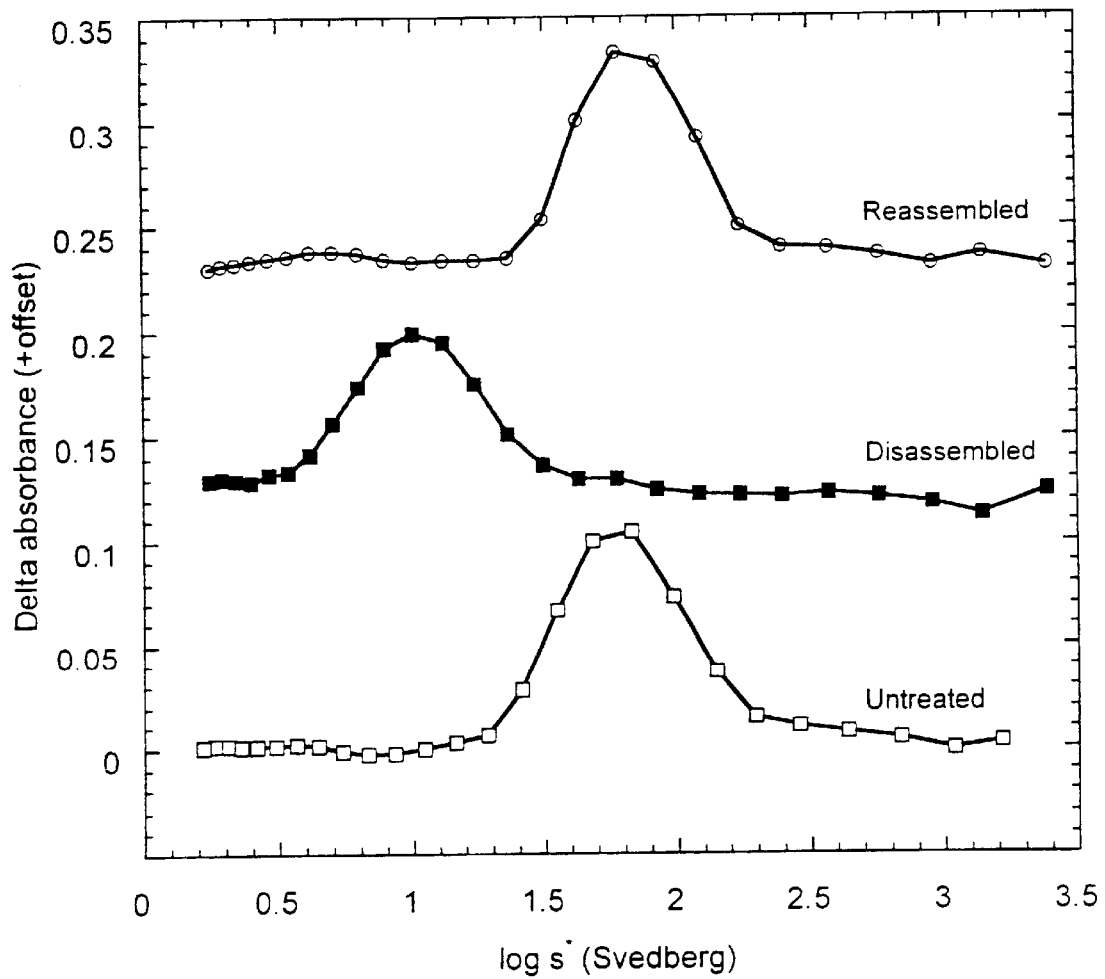
FIG. 1 is a graph showing disassembly and reassembly of HPV 16 VLPs as determined by analytical ultracentrifugation analysis.

This invention relates to a process for producing more stable HPV VLPs which have been found to contribute significantly to the overall stability of an HPV vaccine formulation. The purified HPV VLPs are produced, disassembled into presumably capsomeres, reassembled into VLPs, and then used as the active ingredient in a vaccine formulation.

In accordance with this invention, any type of HPV VLPs may be used as the antigenic portion of the vaccine formulation. The VLPs may contain only L1 protein, or may contain both L1 and L2 protein. The proteins may be of a wild-type amino acid composition, or they may contain mutations. VLPs containing only L1 protein which is of a wild-type amino acid composition are preferred.

The HPVs which are preferred are those associated with disease, including but not limited to: HPV 1, HPV 2, HPV 3, HPV 4, HPV 6a, HPV 6b, HPV 7, HPV 10, HPV11, HPV 16, and HPV 18, HPV 34, HPV 39, HPV 41–44 and HPV 51–55. Preferred HPVs include HPV 6a, HPV 6b, HPV 11, HPV 16, and HPV 18. In addition, the formulations of this invention are suited for combinations of HPV types, including multivalent vaccines containing a plurality of HPV antigens, such as a combination of HPV 6, 11, 16 and 18.

It is preferred that the VLPs be made by recombinant techniques, as is known in the art. It is particularly preferred that the host cell used to make the VLPs is a yeast cell, although other cell types, such as bacterial, insect and mammalian cells are known and currently used as hosts. While not wishing to be bound by theory, it appears that the status of disulfide bonds in the L1 protein in a VLP may differ depending on the host cell used to express the recombinant L1 as well as the subsequent purification method. McCarthy et al 1998, supra describes some disulfide crosslinked L1 trimers in recombinant VLPs produced in insect cells. On the other hand, in accordance with this invention, the disulfide bond status in the L1 protein of VLPs produced in yeast may differ and thus require different conditions for optimal disassembly and reassembly.

For some formulations, an aluminum absorbed product is desired. Generally in this case, the concentration of HPV VLPs which are adsorbed onto aluminum is from about 10–200 mcg/mL for each HPV VLP type. This may be adjusted, depending on such factors as antigenicity of the particular type of HPV, and the presence of multiple types of HPVs in a "cocktail"-type of vaccine.

Disassembly

After the VLPs are produced in the recombinant host cell and purified, they are disassembled by incubating them in a dissociation mixture. Disassembly is primarily driven by the reduction of disulfide bonds with a reducing agent such as dithiothreitol (DTT) in a relatively wide range of ionic strength environments varying from physiological (also referred to as the "low salt process") up to 1.25M NaCl (also referred to as the "high salt process"). The dissociation mixture comprises a reducing agent, a salt, a nonionic surfactant, a metal chelating agent and a buffer.

The reducing agent is preferably dithiothreitol (DTT), although other reducing agents are known and can be used. In the past, others have used other reducing agents (such as beta-mercaptoethanol, $\beta$-ME) to disassemble HPV particles (see, e.g. McCarthy et al, supra), but they have employed a relatively high concentration of reducing agent (5%, or 713 mM of $\beta$-ME). In contrast, one aspect of the present invention is the use of a relatively low concentration of the reducing agent.

For purposes of the specification and claims, the term "relatively low concentration of a reducing agent" means from about 2 mM to 20 mM if using DTT as the reducing agent, or if an alternate reducing agent is employed, the amount of the alternate reducing agent which would have approximately the same effect as employing 2–20 mM DTT. A preferred amount of reducing agent is about 10 mM DTT.

Another important component of the dissociation mixture is the salt. Generally, the ionic strength of the dissociation mixture is maintained by the presence of salts. Almost any salt which can contribute to the control of the ionic strength may be used. Preferred salts which can be used to adjust ionic strength are any physiologically acceptable salts, such as NaCl, KCl, $Na_2SO_4$, $(NH_4)_2SO_4$, sodium phosphate, sodium citrate and mixtures thereof. Particularly preferred salts are: NaCl, KCl, and $Na_2SO_4$, and especially NaCl.

In a low salt embodiment of this invention, the dissociation mixture should have an ionic strength which is approximately physiological. For purposes of this specification and claims, the term "approximately physiological" when referring to a salt, means 0.10–0.20M, and preferably about 0.15–0.18M, and more preferably about 0.16M when employing NaCl as the salt. For other salts which may be used, it is within the skill of the artisan to calculate molarity which would be the equivalent of an approximately physiological NaCl solution.

Alternatively, the dissociation can take place in a high salt environment. As used herein, "high salt" means at least 0.5M salt, and at least 10 mM buffering agents. A preferred range for high salt is 0.5 to 1.25M, if the salt used is NaCl, and a more preferred range is 0.60 to 0.1M. For other salts, it is within the skill of the artisan to determine molarity which would be the equivalent of a 0.5M and 1.25M NaCl solution.

The successful use of a high salt disassembly procedure was quite unexpected-literature reports such as Brady et al, 1977 *Virology* 23: 717–724, Belnap et al 1995 *J. Mol. Biol.* 259: 249–263 and published patent application WO 99/13056 limit salt concentration to less than 0.5M NaCl. Nonetheless, it has been found that the use of a high salt disassembly is advantageous in that the high salt limits possible protein aggregation, results in improved protein mass recovery, and also allows the dis/reassembly treatment to be initiated at the final purification chromatography step, thereby reducing the number of processing steps needed during purification.

It has been surprisingly found that a preferred high salt solution (such as 1.0M NaCl, 10 mM TRIS buffer, pH 8.2, 2 mM EDTA, 0.03% polysorbate 80 and 2–20 mM DTT) results in approximately 100% HPV protein mass recovery in the process. Another high salt solution (0.63M NaCl, 35 mM Phosphate buffer, 100 mM TRIS buffer, pH 8.2, 2 mM EDTA, 0.03% polysorbate 80 and 2–20 mM DTT) is also preferred.

In order to better understand and characterize the effect of the high salt concentration on the effectiveness of HPV VLP disassembly, comparative studies under both high (0.5–1.0M NaCl) and low (physiological) salt disassembly conditions were carried out. Changes in static light scattering intensity were monitored to evaluate the VLP disassembly. It was observed that the results were quite similar for both high salt and physiological salt conditions-complete VLP disassembly occurred within about two minutes of (20 mM) DTT addition. Further the kinetics of disassembly seems controlled by the concentration of reducing agent rather than by salt concentration, with the higher concentration of reducing agent correlating with a faster disassembly at a given temperature and pH.

Other biophysical properties of VLPs disassembled and reassembled in either physiological or high salt were examined. Thermal stability and hydrodynamic size distributions for disassembly/reassembly VLPs generated under both high and low salt conditions are similar. However, the total protein mass recovery was relatively higher (close to 100%) for the disassembled/reassembled HPV VLPs generated with high salt disassembly process.

Another component of the dissociation mixture is a non-ionic surfactant. The non-ionic surfactant may be selected from the group consisting of: Polysorbate 80, Polysorbate 20, polyoxyethylene alkyl ethers, Triton X-100®, Triton X-114®, NP-40®, Span 85 and a member of the Pluronic series of non-ionic surfactants. Polysorbate 80 is particularly preferred. A preferred concentration of Polysorbate 80 is from about 0.01–0.50%, and preferably about 0.01–0.10%, and especially about 0.03%.

The dissociation mixture should be pH controlled by the presence of a buffer. The disassembly of HPV VLPs can take place at a wide range of basic pH such as from above 7.0 to 10. A preferred pH is 8.0–8.5, and preferably about 8.2. A preferred buffer is TRIS at 5–100 mM, preferably 5–15 mM, although other buffers such as phosphate may be used. TRIS is generally preferred, as it provides good pH and ionic strength control in the dissociation mixture conditions. Optionally phosphate buffer may be added at 0–50 mM A metal chelating agents is also present in the dissociation mixture to ensure complete disassembly of VLPs. A preferred metal chelating agent is EDTA at 0.5 to 5 mM, and preferably about 2 mM, although other known chelating agents may be used.

A particularly preferred dissociation mixture comprises approximately 300 mcg/mL HPV VLP protein in a 10 mM TRIS buffer, pH 8.2, additionally containing 0.16M–0.18M NaCl, 10 or 20 mM DTT, 2 mM EDTA and 0.03% Polysorbate 80. Alternatively, the dissociation mixture contains the same amount of protein in 0.63M NaCl, 35 mM phosphate, 100 mM TRIS buffer, pH 8.2, 10 or 20 mM DTT, 2 mM EDTA and 0.03% Polysorbate 80.

One advantage to the process of this invention is that the disassembly step is fairly rapid, and only requires incubation of the VLPs in the dissociation mixture for less than about one hour at room temperature, and times as short as 30–40 minutes can be used. If desired, the dissociation step (as well as other steps of the disassembly/reassembly process) may be performed under sterile conditions. For example, the buffer components may be sterile filtered, and used with sterile protein solutions. In addition, the dis/reassembled HPV VLPs in solution may be sterile filtered prior to use or prior to adsorption to aluminum adjuvant.

After disassembly of VLPs is complete, the reducing agent should be removed. This may be accomplished through the use of a dialysis step or a diafiltration/ultrafiltration step. The dialysis step comprises a dialysis against a solution of salt (physiological strength or, if the high salt process was used, higher concentration of salt such as 1M), non-ionic surfactant, and buffer similar to that present in the dissociation mixture, but at a lower pH than is present in the dissociation mixture. Recommended pH ranges in this dialysis step are from about 6.5–7.5, and preferably about 7.0. One preferred dialysis solution comprises 0.16–0.18 M NaCl, 0.01–0.03% polysorbate 80, 10 mM phosphate at pH 7.0. Another example of a recommended dialysis is a 1:100 dialysis (three changes, 30 minutes each) against a solution of 0.166M NaCl, 10 mM phosphate buffer, pH 7.0. Alternatively, a preferred solution is 1.0 M NaCl, 10 mM phosphate and 0.03% polysorbate 80, pH 7.0.

If needed, additional non-ionic detergent such as polysorbate 80 can be added to the buffer used to remove DTT in order to maintain a sufficient level of nonionic detergent with the protein throughout the process.

Alternatively, the reassembly solution described below could be used to remove the DTT.

With larger volumes, a scalable diafiltration or ultrafiltration setup can be used in place of dialysis procedure.

Reassembly

The next step is to reassemble VLPs. This may be accomplished during the dialysis step described above, during the diafiltration/ultrafiltration step described above, or during a separate, or additional dialysis step, and may take several hours up to about 24 hours. If using a separate dialysis, the dialysis is accomplished using a reassembly buffer comprising: ionic strength salt in the range of 0.5–1.35M NaCl, a metal ion source, a buffer at pH 6.0–6.5.

The salt is preferably the same salt as has been used in the previous steps, although its concentration is preferably higher. For example, if NaCl is used, it should be present at a concentration of 0.5–1.35M, and preferably about 1.0M.

The source of metal ions should be a $Ca^{+2}$ or a $Mg^{+2}$ source, such as $CaCl_2$, or $MgCl_2$ and is present presumably to provide stability to the reassembled VLPs. Zinc may also be used, but typically is less advantageous than the other ions. $CaCl_2$ is preferred. The amount of metal ion should be present is a concentration of about 1–10 mM, preferably about 2 mM.

Glycine or sodium citrate are added as a reassembly buffer component and/or a pH controller. Amounts range from about 20–70 mM, preferably about 50 mM.

The buffer can be the combination of glycine and phosphate, or citrate and phosphate, or citrate alone. The use of phosphate buffer alone is not recommended. A preferred reassembly buffer is 1M NaCl, 2 mM $Ca^{+2}$, 50 mM citrate, pH 6.2 and 0.03% polysorbate 80.

If needed, additional non-ionic detergent such as polysorbate 80 can be added to the reassembly buffer to maintain a sufficient level of nonionic detergent with the protein throughout the process.

With larger volumes, a scalable diafiltration or ultrafiltration setup can be used in place of dialysis procedure.

Buffer Exchange

Finally, any remaining reagents may be removed by dialysis using a final dialysis buffer. One example contains salt (preferably NaCl), and non-ionic surfactant, and optionally histidine. The salt, if NaCl, is preferably present at about 0.25M–1M, more preferably about 0.5M. Histidine may be present at 2–50 mM, preferably about 5–20 mM with a pH 6.0–6.5, and preferably about pH 6.2. The non-ionic surfactant, such as polysorbate 80 or polysorbate 20 may be present at 0.01–0.03%. An alternative preferred buffer exchange is 0.5M NaCl and 0.03% polysorbate 80.

These multiple dialysis steps used to dis/reassemble the HPV VLPs may be also performed with larger scale equipment such as diafiltration and/or ultrafiltration systems. If needed, additional non-ionic detergent such as polysorbate 80 can be added to any of the dis/reassembly buffers to maintain a sufficient level of nonionic detergent with the protein throughout the process.

If desired, the dis/reassembled HPV VLPs may be adsorbed onto an aluminum adjuvant using known techniques.

Optionally, the stability of the reassembled VLP formulation may be further enhanced by the addition of polyanionic, polymeric excipients. As used throughout the specification and claims, the term "polyanionic polymer" is meant to refer to compounds which have either a single long chain, or those with multiple cross linked chains; either type possessing multiple negative charges along the chain(s) when in solution. Examples of polyanionic polymers include: proteins, polyanions, peptides and poly-nucleic acids. Specific stabilizers may be selected from the group consisting of: carboxymethyl cellulose (particularly 10–800 cps),heparin (6–30 kDa), poly-amino acids (2–100 kDa) such as poly(Glu), Poly(Asp), and Poly(Glu, Phe), oxidized glutathione [Glu-Cys-Gly]$_2$ (613 Da), poly-nucleotides such as polycytidylic acid (200–700 kDa), and polyadenylic acid (200–700 kDa), RNA, DNA, and serum albumins.

The concentration of the polyanionic polymeric excipient, when present, is from about 0.01% to about 0.5%, particularly about 0.05–0.1% (by weight/volume), although the addition of even a ten fold lower amount of polyanionic excipients (for example, 0.01% albumin, DNA or heparin) still provides enhanced stability to untreated HPV VLP-aluminum formulations.

A typical vaccine formulation includes:

1) aluminum absorbed product containing 10–200 mcg/mL of each HPV VLP type and 0.15–0.32M saline; 2) 5–10 mM histidine, pH 6.2; and 3) 0.005–0.03% non-ionic surfactant.

The resulting HPV vaccine formulations of this process are stable at 2–8° C. to room temperature for at least 6 months (study ongoing) as illustrated in FIG. 7.

Another aspect of this invention is the use of a formulation buffer to provide for stable, long-terms storage of vaccines made with the disassembled/reassembled VLPs. The formulation buffer comprises 0.15–0.32M NaCl, 5–10 mM histidine, pH 6.2, and 0.005–0.015% polysorbate 80. These vaccine formulations are stable at various temperature ranges (from 4–30° C.) for up to at least six months. The following non-limiting Examples are presented to better illustrate the invention.

EXAMPLE 1

A frozen solution of yeast derived recombinant L1 protein HPV 16 VLP (greater than 95% protein purity) in 0.5M NaCl, 0.003% Polysorbate 80, pH targeted at approximately 6.2, was used for most of these experiments. HPV 6a VLPs and HPV 11 VLPs were in 0.5M NaCl, 0.03% Polysorbate 80. The HPV 18 VLPs were at 0.5 M NaCl, 0.01% Polysorbate 80. Some of the studies utilized HPV 6a, 11, and 16 VLPs in 75 mM phosphate buffer at pH 7 containing 1.25M NaCl.

Release of HPV VLPs from Aluminum Adjuvant for Subsequent in Vitro Analysis

To release HPV VLPs from the aluminum adjuvant, an aluminum dissolution method was developed which included dilution of HPV-aluminum formulation into a high salt solution containing citrate and polysorbate 80. The HPV VLP samples from the aluminum dissolution method are directly subjected to an in vitro antigenicity assay using BIAcore analysis.

In vitro antigenicity assay. The HPV VLP samples from the aluminum dissolution method were in a stabilizing solution of pH 6–6.5 and high ionic strength (about 0.5M–1M NaCl, 0.1M sodium citrate) containing 0.02% Polysorbate 80. The samples are directly subjected to BIAcore analysis without further dilution (utilizing HPV VLP type specific neutralizing antibody). Solution samples (no aluminum adjuvant) were diluted to a target concentration in about 0.5–1M NaCl before BIAcore analysis. All in vitro antigenicity data are referenced to a frozen HPV VLP control sample (not aluminum adsorbed).

Protein concentration analysis. The protein concentration of HPV VLPs in both bulk solutions and formulated samples (after aluminum dissolution) were determined by UV absorbance spectra measurement at ambient temperature using a HP 8452A Diode Array spectrophotometer and a cuvette with a path length of 1 cm. The sample volumes used were 100–250 microliters. The protein concentration was calculated using a multi-component second derivative analysis technique. For some experiments, protein concentration was also determined by BCA colorimetric analysis.

Hydrodynamic size analysis. The hydrodynamic size of untreated and dis/reassembled HPV VLPs were determined by dynamic light scattering, analytical ultracentrifugation, and SEC-HPLC.

Dynamic light scattering measurements were performed at ambient temperature using a Malvern 4700 Light Scattering System at 90°. The apparent hydrodynamic size of HPV VLPs was determined as Z-average hydrodynamic diameter. Each of the values represents the mean of five measurements of the same sample.

Sedimentation velocity experiments were performed using Beckman XLI analytical ultracentrifuge with UV detection at 280 nm. Two different methods were used to determine the sedimentation coefficient including fixed and variable speed modes.

SEC-HPLC measurements were performed at ambient temperature using a Waters/Millennium 2690 system with UV and fluorescence detectors. A PL-GFC 4000 Å column (preconditioned with HPV VLPs) was used at a flow rate of 0.4 ml/minute using 750 mM NaCl, 25 mM phosphate buffer (pH 7) as mobile phase.

Electron microscopic analysis. Transmission Electron Microscopy (TEM) was performed using negative staining. Samples were fixed and stained with phosphotungstic acid and examined in a JEOL 1200 EX Transmission Electron Microscope. Micrographs were taken of random areas with samples prepared multiple times at a magnification between 30,000×and 40,000×. An additional 3-fold magnification was introduced in developing the prints from the negatives.

Real time and accelerated storage stability studies. HPV-aluminum formulation storage stability studies were carried out. The temperature of stability studies was generally 2–8, 15, 25, 30 and 37° C. Previous conformational integrity data (not shown) with circular dichroism and fluorescence spectroscopy has shown that increasing the temperature above 40–45° C. induces significant conformational changes in the L1 protein of HPV VLP, a condition which definitely needs to be avoided in accelerated storage stability studies.

HPV VLP thermal stability was also evaluated with turbidity assays which were carried out using a HP 8452A Diode Array spectrophotometer equipped with a HP 845X UV-Visible system software and a temperature control system. The light scattering of the solutions (due to protein aggregation) was followed at 350 nm under the kinetic mode of the program by increasing the temperature from 24° C. to 74° C. at a controlled rate.

Mouse potency testing—In vivo immunogenicity of HPV VLPs was evaluated in BALB c mice. HPV VLPs samples were adsorbed onto aluminum adjuvant, diluted to several target concentrations with aluminum adjuvant and injected into mice. Sera were collected and analyzed for antibody levels by ELISA assay.

EXAMPLE 2
Disassembly and Reassembly of HPV 16 VLPs as Determined by Analytical Ultracentrifugation Analysis As seen in FIG. 1, HPV 16 VLPs are disassembled after incubation in a pH 8.2 buffer containing 10 mM TRIS or phosphate, 0.166M NaCl, 2 mM EDTA, and 2 mM DTT at room temperature for 20 minutes (middle curve). The disassembled HPV 16 sample shows a peak at smaller S value expected for L1 capsomeres, suggesting a size of HPV L1 protein pentamers. The top curve shows that the disassembled HPV 16 (capsomeres) was then reassembled into VLPs by dialyzing into a pH 6.2 buffer containing 10 mM sodium phosphate, 0.5 to 1M NaCl, 2 mM calcium chloride in the presence of either glycine or citrate. The bottom curve shows the untreated HPV 16 VLPs.

EXAMPLE 3
Particle Size Distributions of Dis/Reassembled HPV 16 VLPs

Figure 2:
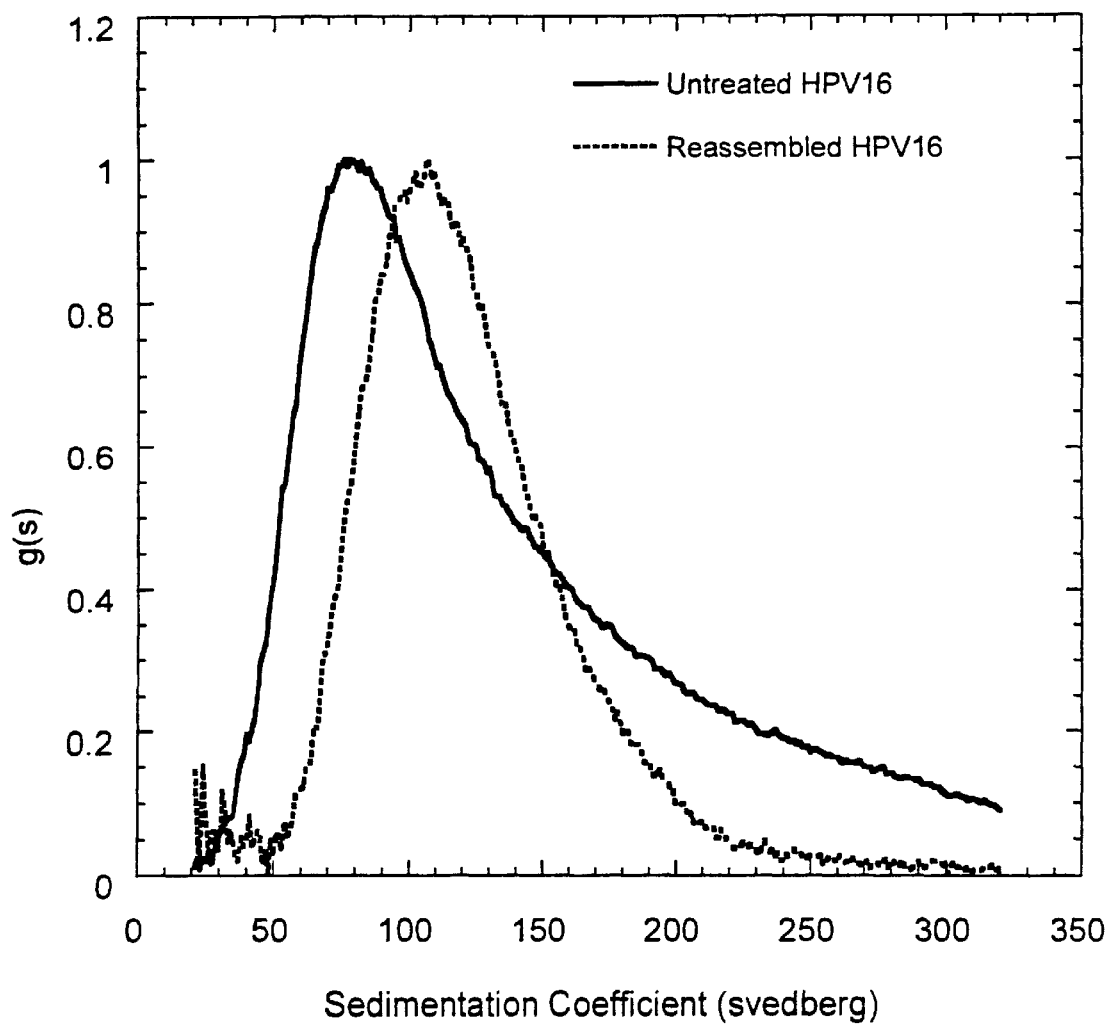
FIG. 2 is a graph showing particle size distributions of dis/reassembled HPV 16 VLPs (dashed line) and untreated HPV 16 VLPs (solid line) as determined by analytical ultracentrifugation analysis.

FIG. 2 shows particle size distributions of HPV 16 VLPs which were disassembled and reassembled as described in Example 2 (dashed line) and untreated HPV 16 VLPs (solid line) as determined by analytical ultracentrifugation analysis. The data reveal that dis/reassembled HPV 16 VLPs are larger and have a more homogenous distribution, as judged from the positions and widths of the peaks, respectively. Electron microscopy (EM) analysis confirms the analytical ultracentrifugation analysis; it shows that the dis/reassembled VLPs are more homogenous and exist as rounder particles of uniform size with mean diameter of approximately 80–85 nm (EM data not shown). Untreated samples appear to be smaller and with more heterogeneous shape and size distribution with an mean size around 50–68 nm. Similarly, a later set of data shows untreated HPV 16 VLPs to have a mean size of approximately 40 nm, while the reassembled HPV 16 VLPs have a mean size of approximately 60 nm.

EXAMPLE 4
Accelerated Stability (37° C.) of HPV 16 VLP-Aluminum Vaccine Formulations as Determined by BIAcore Analysis The dis/reassembled HPV 16 VLPs as well as untreated HPV 16 VLPs were adsorbed onto aluminum adjuvant (at 160 mcg/mL protein and 450 mcg/mL Al) and formulated in 0.32M NaCl, 10 mM histidine, 0.015% polysorbate 80, pH 6.2. The in vitro antigenicity of the samples were assayed at identified times by BIAcore analysis.

Figure 3:
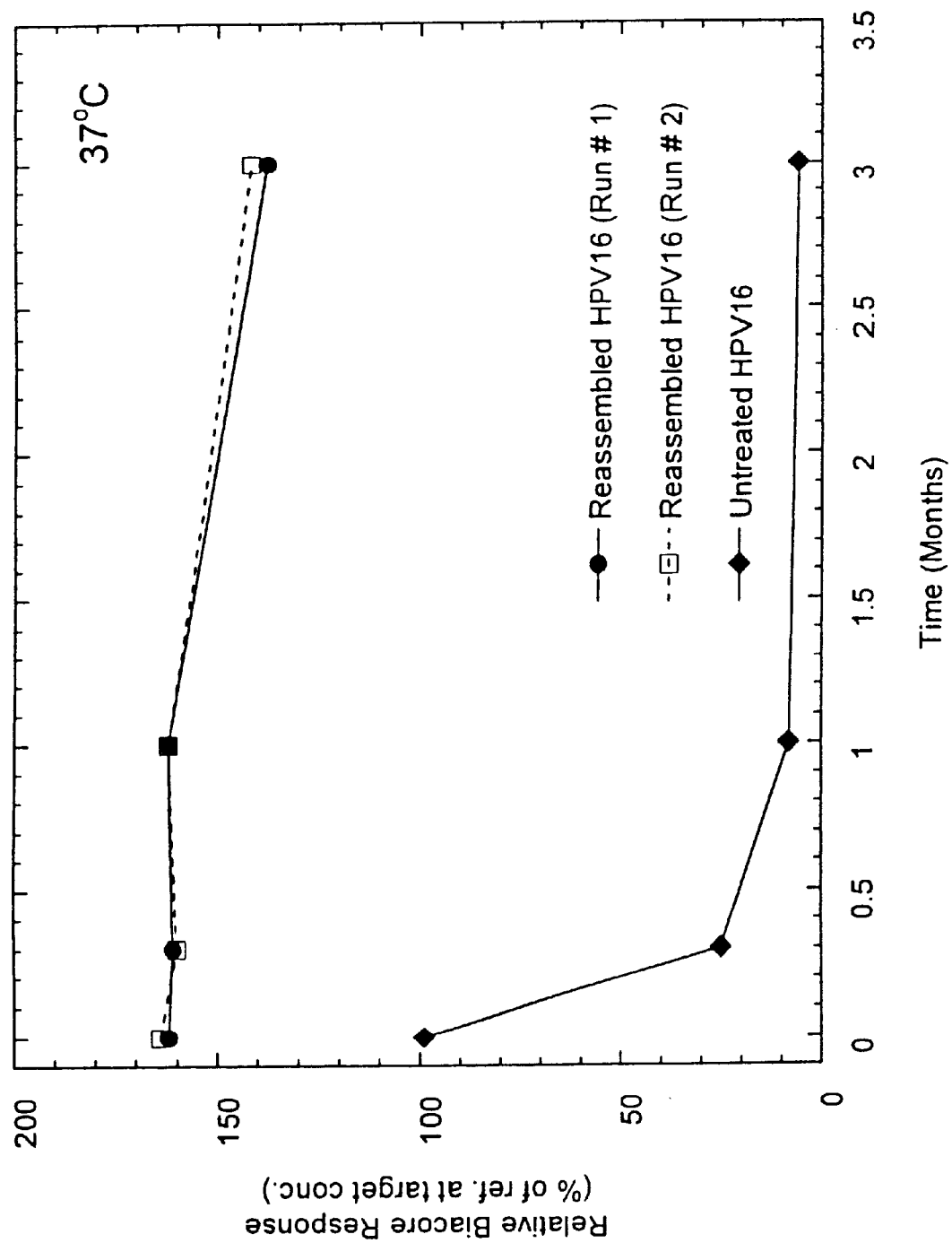
FIG. 3 is a graph showing accelerated storage stability (37° C.) of HPV 16-aluminum vaccine formulations as determined by in vitro antigenicity via BIAcore analysis.

In FIG. 3, disassembled and reassembled HPV 16 VLPs are shown with filled circles and open squares; and untreated are filled diamonds. Run 1 contained citrate and Run 2 has glycine in the reassembly buffer. The data demonstrate the dis/reassemble process results in a significant and dramatic enhancement in accelerated storage stability of aluminum adjuvant adsorbed HPV 16 VLPs as compared to untreated HPV VL Ps. No loss in in vitro antigenicity of aluminum adsorbed dis/reassembled HPV VLPs was observed in similar experiments performed at 25° C. and 4° C. after three months.

Figure 4:
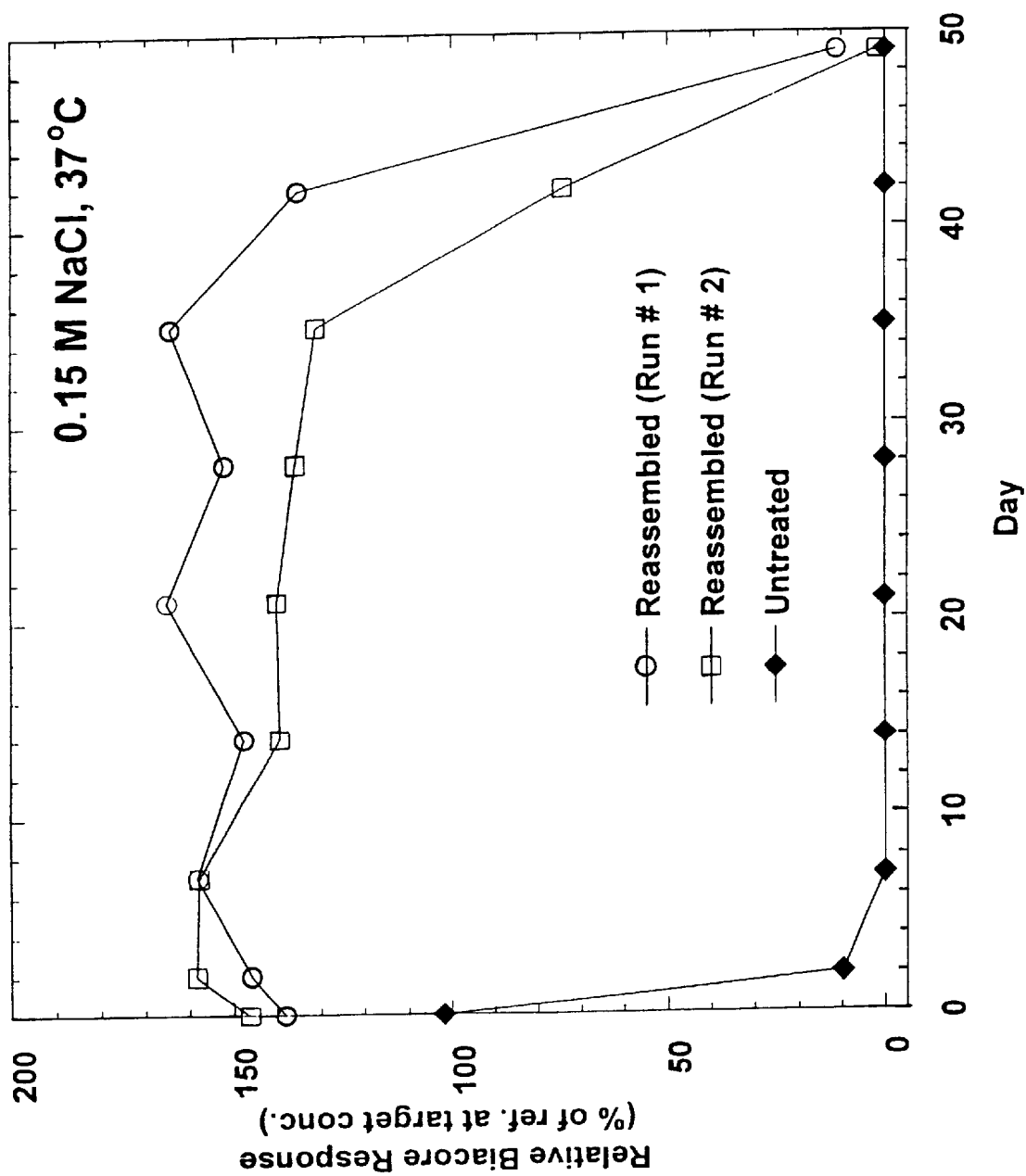
FIG. 4 shows the accelerated storage stability of HPV 16 VLPs in physiological salt solution as determined by in vitro antigenicity via BIAcore analysis.

EXAMPLE 5
Accelerated Stability (37° C.) of HPV 16 VLPs in Solution in Physiological Salt Solution as Determined by BIAcore Analysis 80 mcg/ml of dis/reassembled HPV 16 VLPs as well as untreated HPV 16 VLPs were incubated in 0.15M NaCl, 10 mM histidine, 0.015% polysorbate 80, pH 6.2 at 37° C. The in vitro antigenicity of the samples were assayed at identified times by BIAcore analysis. The data demonstrate the dis/reassemble process results in a significant enhancement in accelerated storage stability of HPV 16 VLPs as compared to untreated HPV VLPs. This is shown in FIG. 4, where disassembled and reassembled VLPs are in open circles and open squares; untreated VLPs are shown in filled diamonds. Run 1 contains citrate and Run 2 has glycine in the reassembly buffer.

EXAMPLE 6
Effect of Dis/Reassembly Process Treatment on the Thermal Stability of Different Lots of HPV 16 VLPs as Determined by Monitoring Thermal-induced Turbidity Formation (Aggregation) by UV Spectroscopy (Cloud Point Analysis)

Figure 5:
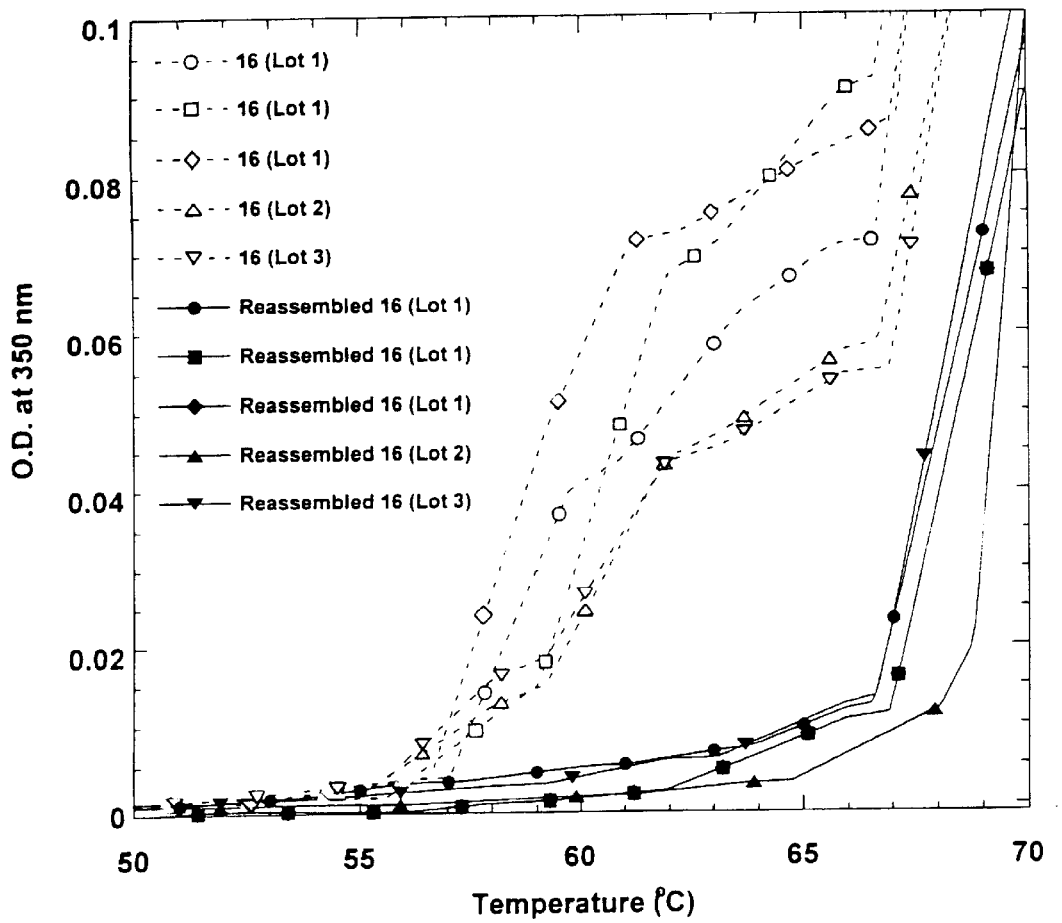
FIG. 5 shows the effect of dis/reassembly treatment on the thermal stability of different lots of HPV 16 VLPs as determined by monitoring thermal-induced aggregation by UV turbidity (cloud point analysis).
Figure 6A:
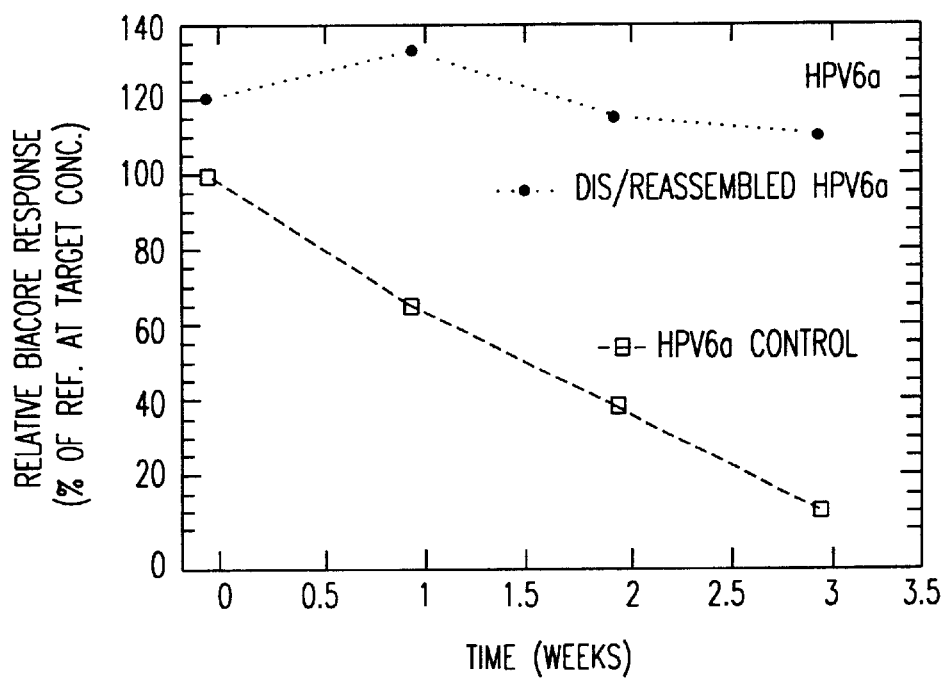
FIGS. 6A–D show the accelerated storage stability (37° C.) of four different types (HPV 16, 11, 6a, 18) of dis/reassembled HPV VLPs as well as untreated control HPV VLPs in solution as determined by in vitro antigenicity via BIAcore analysis.
Figure 6B:
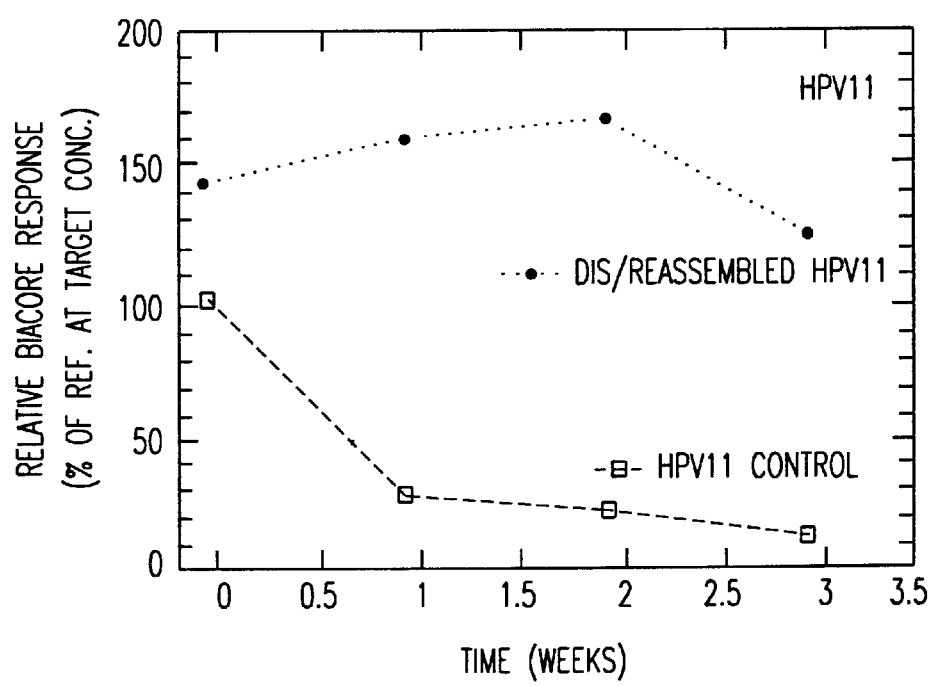
Figure 6C:
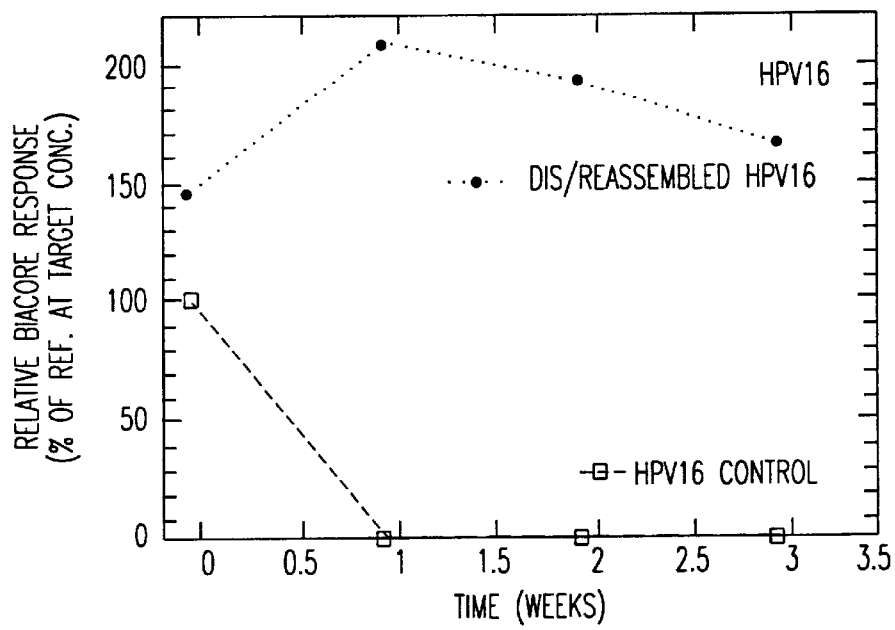
Figure 6D:
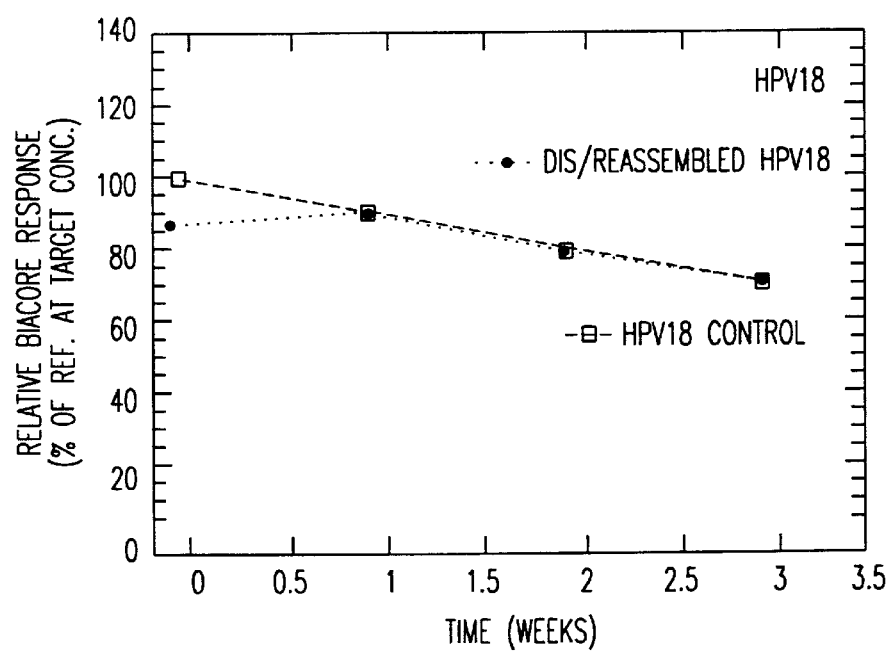
Figure 7A:
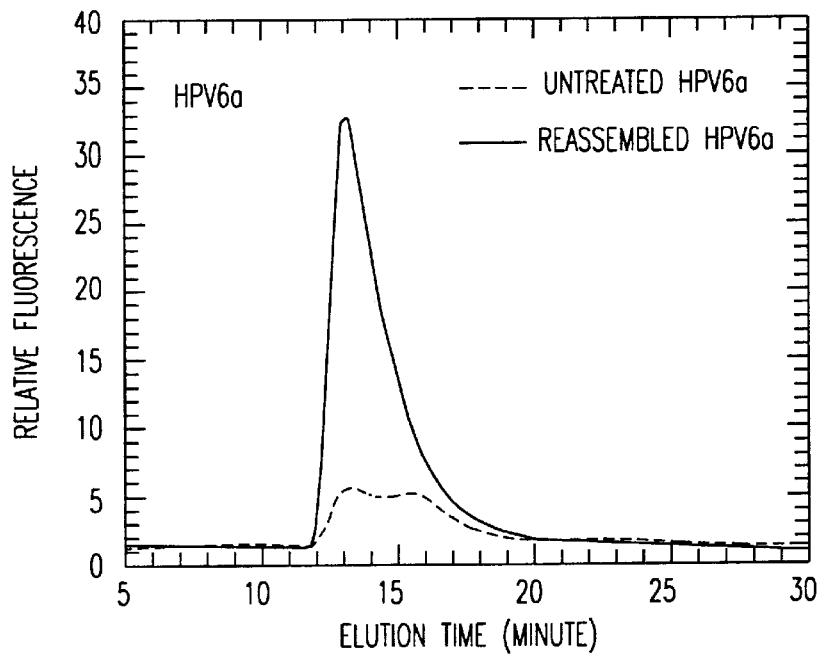
FIGS. 7A–D show the accelerated storage stability of four different types (HPV 16, 11, 6a, 18) of dis/reassembled HPV VLPs as well as untreated control HPV VLPs absorbed on aluminum adjuvant. The samples were assayed for in vitro antigenicity via BIAcore analysis after treated in citrate solution to release the antigen from aluminum adjuvant.
Figure 7B:
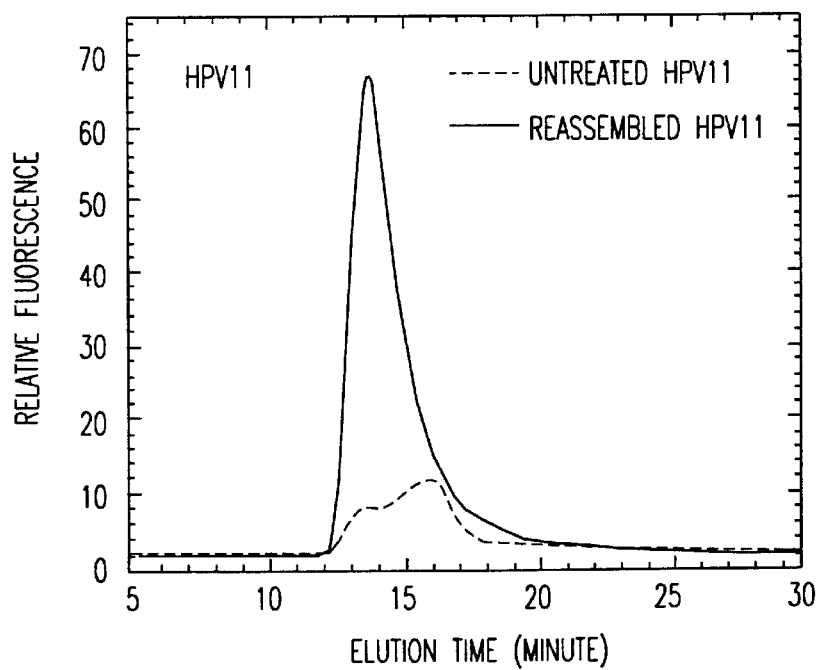
Figure 7C:
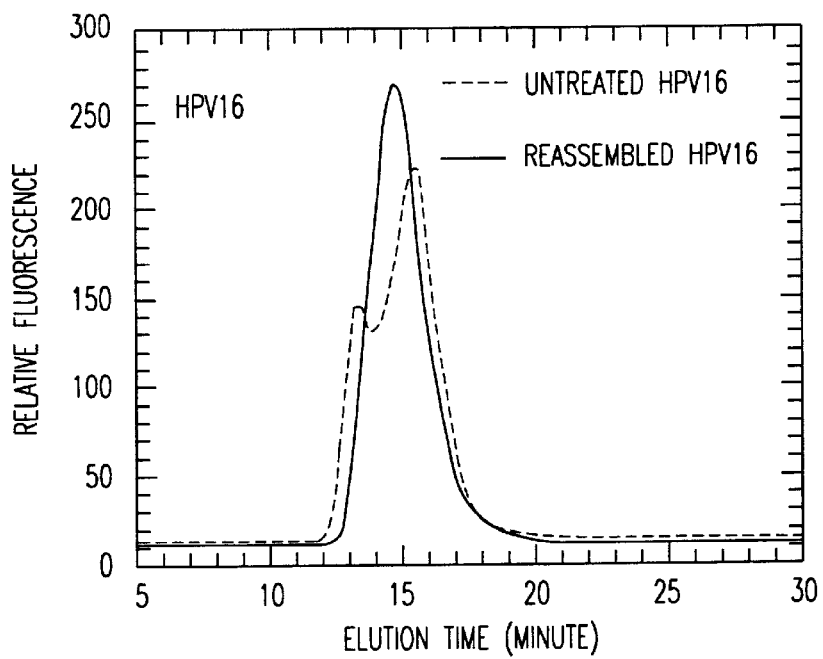
Figure 7D:
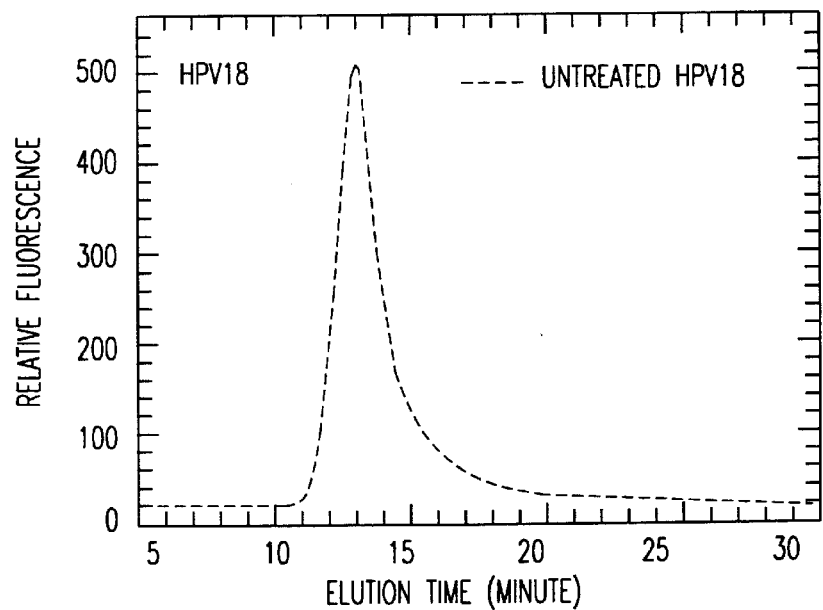
Figure 8A:
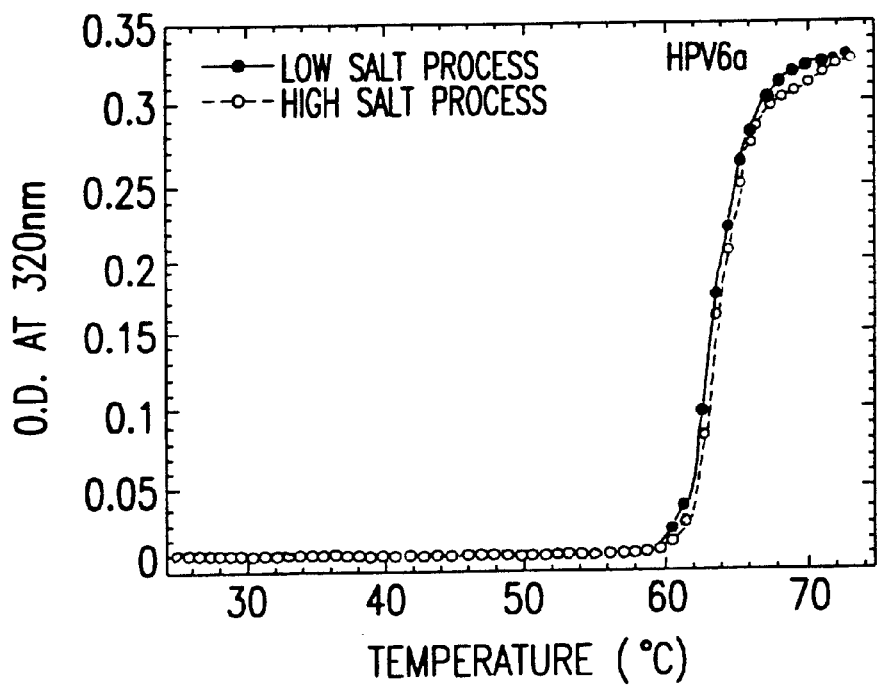
Figure 8B:
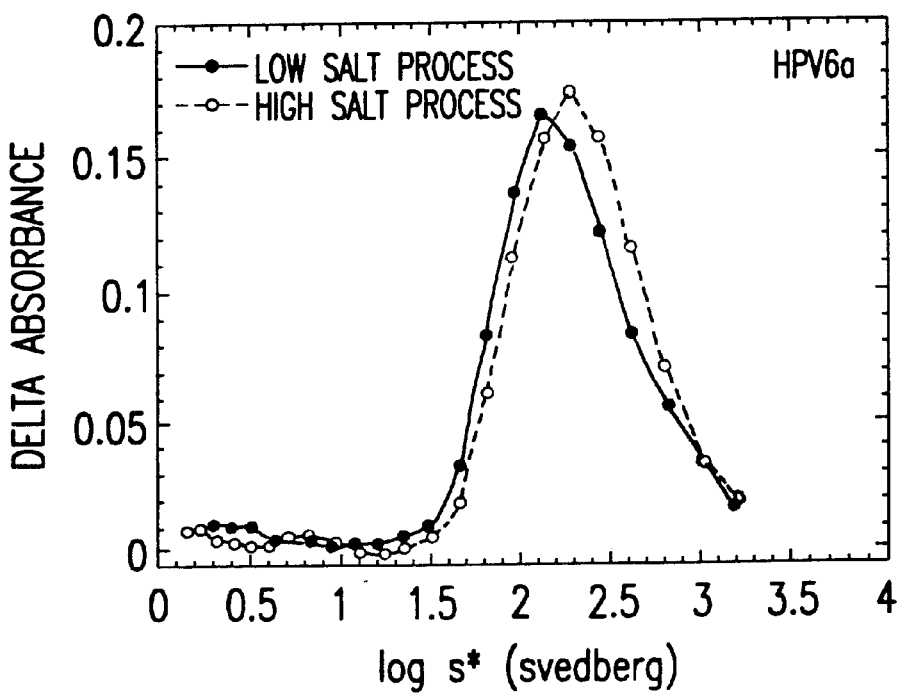
Figure 8C:
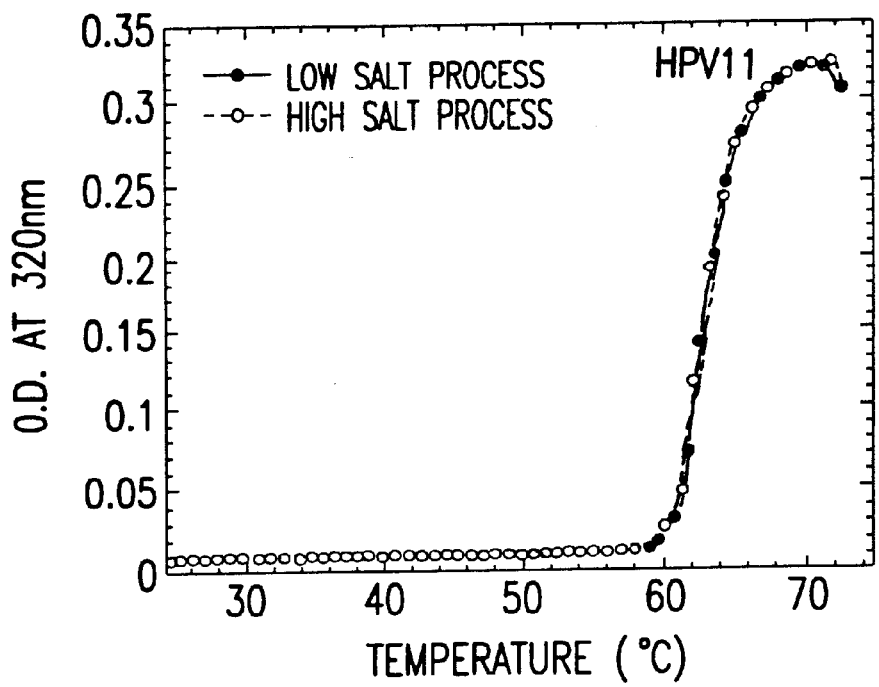
Figure 8D:
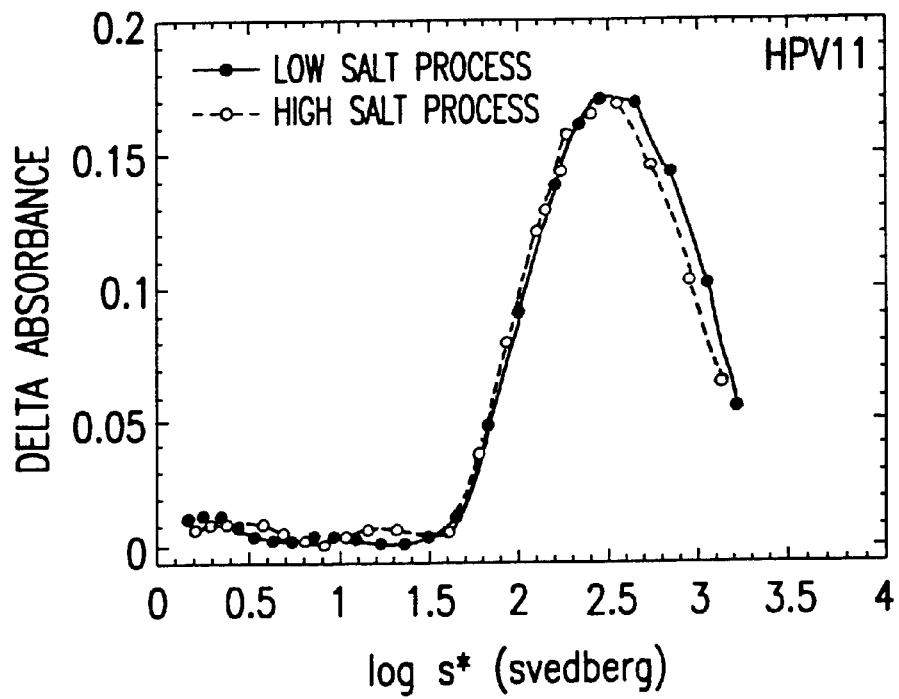
Figure 8E:
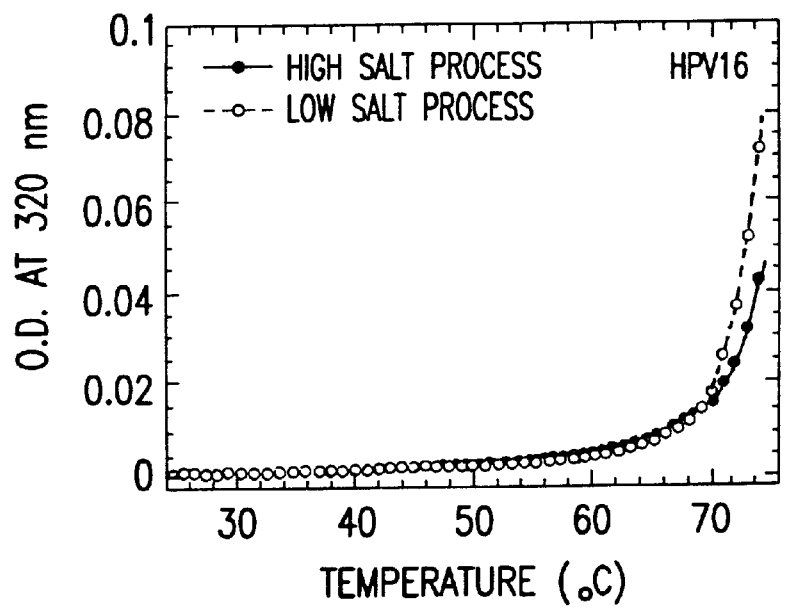
Figure 8F:
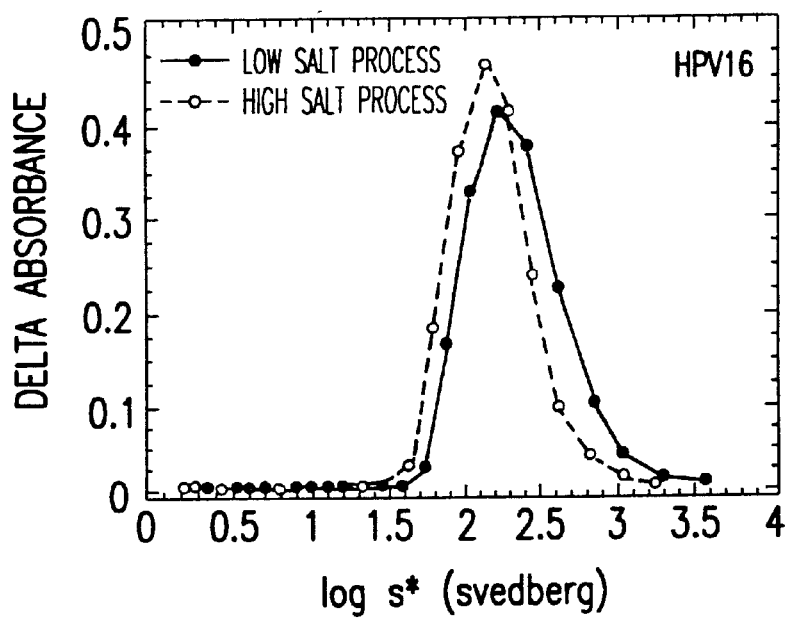
Figure 9A:
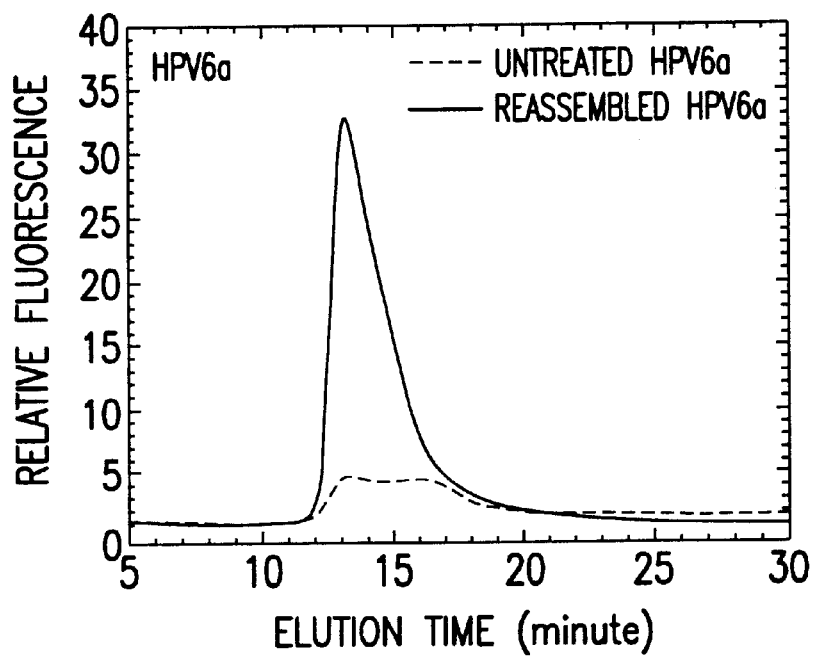
FIGS. 9A–D are the particle size distribution and surface affinity of untreated and dis/reassembled HPV VLPs as measured by SEC-HPLC analysis.
Figure 9B:
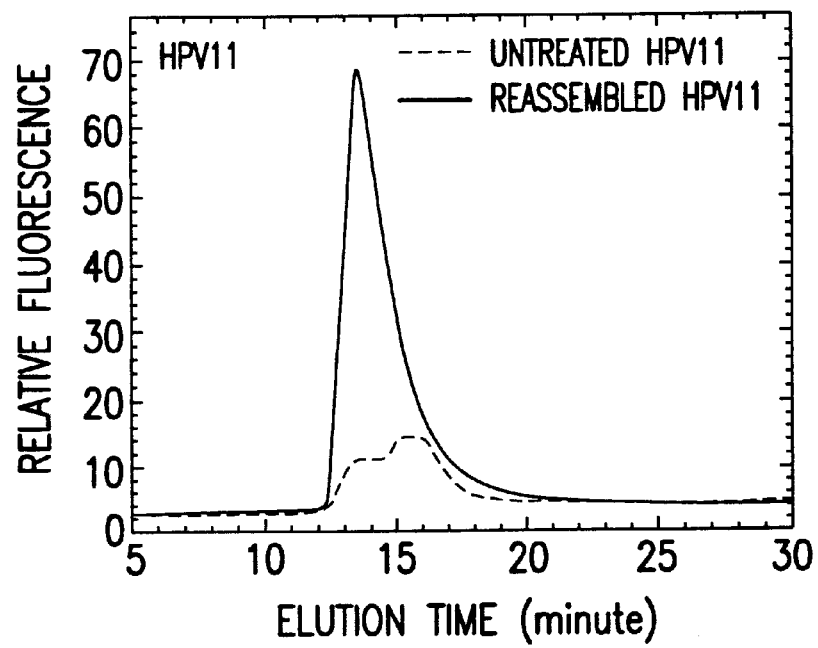
Figure 9C:
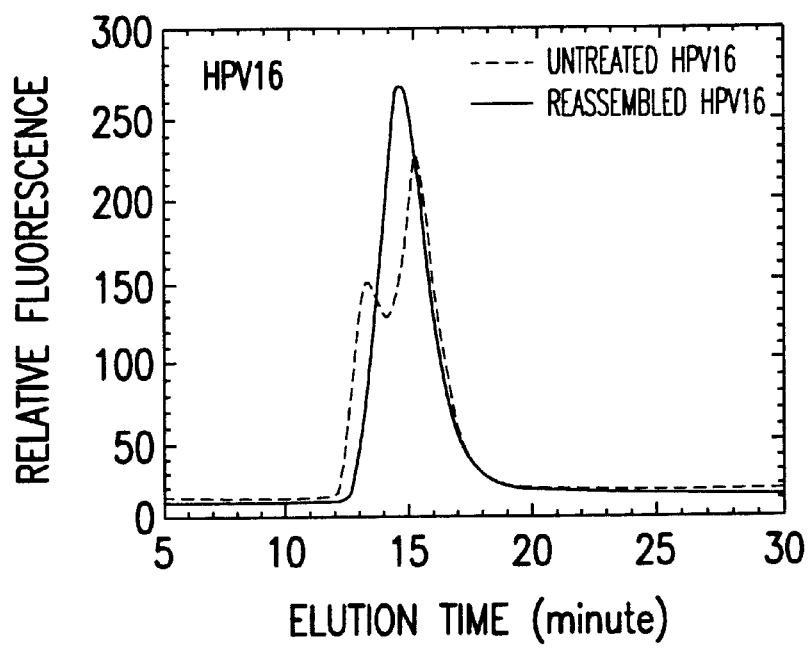
Figure 9D:
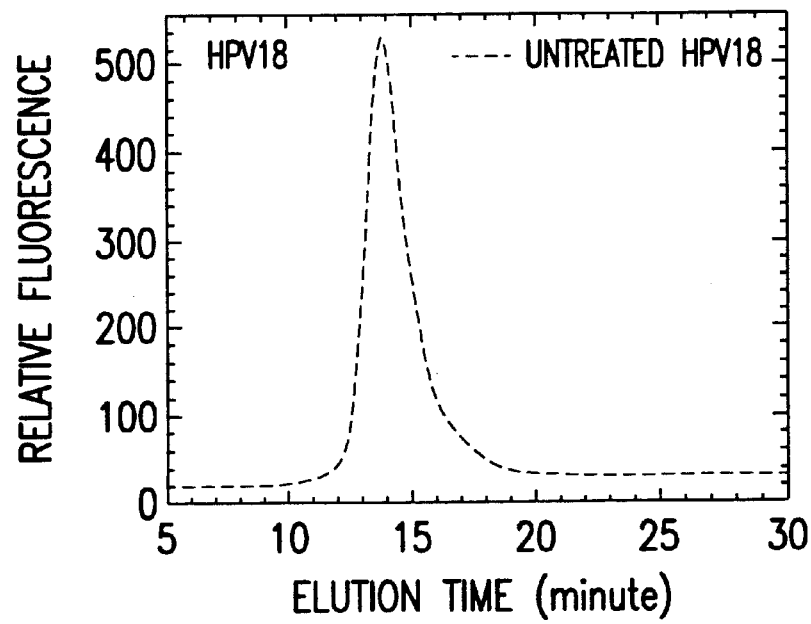

A standard cloud point protocol was applied to the samples: heat from 24° C. to 74° C. at a controlled rate with optical density of the solution being monitored at 350 nm. As shown in FIG. 5, three different lots of HPV 16 VLPs (lots 1,2,3) were analyzed before (dash lines and open symbols) and after (solid lines and filled symbols) dis/reassembly treatment. Among these samples HPV 16 VLPs (lot 1) was tested three times. The data demonstrate that dis/reassembly process treatment results in a significant enhancement of the intrinsic stability of HPV 16 VLPs against heat-induced aggregation. In addition to the thermal stability enhancements, the dis/reassembly process treatment also results in a more consistent and homogeneous stability profile.

EXAMPLE 7

The in vitro antigenicity of untreated and dis/reassembled was further evaluated with a lot of HPV 16 VLPs in which both untreated and dis/reassembled VLPs were evaluated before and after adsorption to aluminum adjuvant. The in vitro antigenicity was measured by BIAcore analysis and the protein concentration by UV spectroscopy and BCA colorimetric assay. The antigen to protein ratio was then determined for both untreated and dis/reassembled HPV 16 VLPs. The in vitro antigenicity of the dis/reassembled HPV 16 VLPs was enhanced by about 50%. For example, the antigen to protein ratio for dis/reassembled vs. untreated HPV 16 VLPs was 1.7 with a range of 1.5–1.9. This observation was confirmed by EIA analysis (mean of 1.6 and range of 1.4–1.8) and IVRP analysis (mean 1.4 and range of 1.3–1.5).

The in vivo immunogenicity of untreated and dis/reassembled aluminum adsorbed HPV 16 VLPs was evaluated with a mouse potency test. This test generates an ED50 value representing the dose (mcg) of HPV VLPs in which more than 50% of the mice seroconvert. The in vivo immunogenicity of the dis/reassembled HPV 16 VLPs was equivalent to, or better than, the untreated HPV 16 VLPs. One experiment shows an ED50 value of 0.034–0.062 for two dis/reassembled samples vs. an ED50 value of 0.146 for the untreated sample. In a second mouse experiment, an ED50 of <0.0125 was obtained for three dis/reassembled HPV VLP samples vs. an ED50 value of 0.074 for the untreated sample.

EXAMPLE 8

Accelerated Stability (37° C.) of Untreated and Dis/Reassembled HPV VLPs in Solution and on Aluminum Adjuvant as Determined by BIAcore Analysis 80 mcg/mL HPV VLPs were incubated in solution containing 0.32M NaCl, 10 mM histidine, 0.015% Polysorbate 80, pH 6.2 at 37° C. Samples were assayed for in vitro antigenicity by BIAcore at times indicated on FIG. 6. The data indicate that the dis/reassembly treatment results in a dramatic stability enhancement for HPV VLP types 6a, 11, and 16 in solution during accelerated storage stability testing. The untreated HPV 18 VLPs show a stability profile similar to the dis/reassembled VLPs for the other three types. No significant stability enhancement is observed with treatment of the UPV 18 VLPs probably due to the inability of the dis/reassembly treatment to affect HPV 18 VLPs (data not shown). The samples used for this study are generated with low salt disassembly process. The protein mass recovery for the four types across the dis/reassembly treatment was approximately 85–95% for HPV 11, 16 and 18 VLPs and approximately 60–70% HPV 6a VLPs. The yield across dis/reassembly treatment seems to be affected by the quality of the specific lot of HPV VLP in terms of VLP aggregation. The protein mass yield across dis/reassembly treatment increases to nearly 100% when the disassembly process take places under high salt conditions. Analysis of the dis/reassembled HPV VLPs by analytical ultracentrifugation suggests that the dis/reassembly treatment results in nearly quantitative reassembly of capsomeres into VLPs.

FIG. 7 shows the storage and accelerated stability of HPV VLPs absorbed on aluminum adjuvant in which 400 mcg/mL HPV VLPs were adsorbed on 450 mcg/mL aluminum adjuvant and incubated in a solution containing 0.32M NaCl, 10 mM histidine, 0.015% Polysorbate 80, pH 6.2 at 4° C., 15° C., 25° C., 30° C. and 37° C. Samples were assayed for in vitro antigenicity by BIAcore at the times indicated on the figure after treatment in a citrate solution to release the antigen from the aluminum adjuvant. The data indicate that the dis/reassembly treatment results in a dramatic stability enhancement for aluminum adsorbed HPV VLP types 6a, 11, and 16 in accelerated storage stability testing. The untreated HPV 18 VLPs show a stability profile similar to the dis/reassembled VLPs for the other three types. No significant stability enhancement is observed with disassembly/reassembly treatment of the HPV 18 VLPs.

EXAMPLE 9

Thermal stability and hydrodynamic size distribution of reassembled HPV 6a, HPV 11 and HPV 16 VLPs, prepared by both the low salt disassembly process and high salt disassembly process. Samples were evaluated by cloud point and analytical ultracentrifugation analysis. In the low salt process, HPV VLPs are disassembled in 0.166 M NaCl, 10 mM TRIS solution (pH 8.2) while in the high salt process, HPV VLPs are disassembled in 0.63 M NaCl, 35 mM Phosphate, and 100 mM TRIS solution (pH 8.2). Both solutions also contain EDTA and polysorbate 80. The data, as seen in FIG. 8 show that the disassembled/reassembled HPV VLPs prepared by the low and high salt processes are similar regarding their thermal stability and hydrodynamic size distribution for HPV VLPs types 11, 6a and 16.

EXAMPLE 10

Particle Size Distribution and Surface Affinity of HPV VLPs as Measured by SEC-HPLC Analysis Dis/reassembled (FIG. 9, solid line) and untreated (dash line) HPV VLPs (Types 11, 16 and 6a) were analyzed on 4000 A GPC size exclusion column. Single peak was obtained from dis/reassembled HPV VLPs compared to a more heterogeneous distribution of untreated HPV VLPs. The monomer peaks of dis/reassembled HPV VLPs have a smaller elution volume than the monomer peaks of untreated HPV VLPs suggesting a relatively larger particle size for the dis/reassembled VLPs. The relatively larger total peak areas of dis/reassembled HPV VLPs indicate a higher recovery rate of dis/reassembled VLPs suggesting that dis/reassembled VLPs have lower affinity to the column than untreated VLPs. Untreated HPV 18 VLPs show a SEC HPLC profile similar to the dis/reassembled VLPs for the other three types.

What is claimed is:

1. A process for making a storage stable human papillomavirus (HPV) vaccine comprising HPV virus-like particles (VLPs), the process comprising the steps of:
   (a) incubating VLPs in a low salt dissociation mixture for less than about one hour, the dissociation mixture comprising:
      0.1–0.2M NaCl,
      2–20 mM DTT,
      0.01–0.5% Polysorbate 80,
      0.5–5 mM EDTA, and
      5–15 mM TRIS buffer at pH 7–10 to produce disassembled VLPs;
   (b) optionally removing the DTT from the dissociation mixture by diafiltration, ultrafiltration or by dialysis against a dialysis buffer comprising:
      0.1–0.2M NaCl,
      0.01–0.05% Polysorbate 80, and
      a phosphate buffer at a pH 6.5–7.5;
   (c) reassembling the disassembled VLPs using by diafiltration, ultrafiltration or by dialysis against a reassembly buffer, the reassembly buffer comprising:
      0.5–1.35M NaCl,
      0.5–5 mM Ca+2 or 0.5–5 mM Mg+2,
      pH 6.0–6.5 buffer selected from the group consisting of 20–70 mM sodium citrate; 20–70 mM glycine and phosphate; and 20–70 mM citrate and phosphate; and
   (d) further purifying the reassembled VLPs using by diafiltration, ultrafiltration or by dialysis against a final buffer, the final buffer comprising 0.25–1M NaCl, 5–20 mM histidine, pH 6–6.5.

2. A method according to claim 1 further comprising:
   (e) adsorbing the reassembled VLPs from step (d) onto aluminum adjuvant.

3. A method according to claim 1 wherein the VLPs are selected from the group consisting of: HPV 6a, HPV 6b, HPV 11, HPV16, HPV 18, and combinations thereof.

4. A method according to claim 1 wherein the VLPs of step (a) are incubated for 30–40 minutes.

5. A method according to claim 1 wherein the dissociation mixture of step (a) comprises:
   0.16–0.18M NaCl,
   2–20 mM DTT,
   0.01–0.03% Polysorbate 80,
   0.5–5 mM EDTA, and
   5–15 mM TRIS buffer, pH 8.2

6. A method according to claim 1 wherein the buffer of step (b) comprises
0.16–0.18M NaCl,
0.01–0.03% Polysorbate 80, and
10 mM phosphate at pH 7.0.

7. A method according to claim 1 wherein the reassembly buffer comprises:
1.0M NaCl,
2 mM Ca+2,
a pH 6.2 buffer selected from the group consisting of: 50 mM sodium citrate, 50 mM glycine and phosphate, and 50 mM citrate and phosphate.

8. A method according to claim 1 wherein the final buffer of step (d) comprises 0.5M NaCl and 10 mM histidine, pH 6.2.

9. A method for making a storage stable human papillomavirus (HPV) vaccine comprising HPV virus-like particles (VLPs), the process comprising the steps of:
  (a) incubating VLPs in a high salt dissociation mixture for less than about an hour, the dissociation mixture comprising:
    0.5–1.25M NaCl,
    2–20 mM DTT,
    0.01–0.05% Polysorbate 80,
    0.5–5 mM EDTA,
    5–100 mM TRIS buffer, and
    0–50 mM phosphate buffer at pH 7–10 to produce disassembled VLPs;
  (b) optionally removing the DTT from the dissociation mixture by diafiltration, ultrafiltration or by dialysis a dialysis against a buffer comprising:
    at least 1M NaCl,
    0.01–0.05% Polysorbate 80
    a phosphate buffer at pH 6.5–7.5;
  (c) reassembling the disassembled VLPs by diafiltration, ultrafiltration or by dialysis against a reassembly buffer, the reassembly buffer comprising
    0.5–1.35M NaCl,
    0.5–5 mM Ca+2 or 0.5–5 mM Mg+2,
    pH 6–6.5 buffer selected from the group consisting of: 20–70 mM sodium citrate, 20–70 mM glycine and phosphate, and 20–70 mM citrate and phosphate; and
  (d) further purifying the reassembled VLPs using by diafiltration, ultrafiltration or by dialysis against a final buffer, the final buffer comprising:
    0.25–1M NaCl, and
    5–20 mM histidine, pH 6–6.5.

10. A method according to claim 9 further comprising:
  (f) adsorbing the reassembled VLPs from step (d) onto aluminum adjuvant.

11. A method according to claim 9 wherein the VLPs are selected from the group consisting of: HPV 6a, HPV 6B, HPV 11, HPV 16, HPV 18, and combinations thereof.

12. A method according to claim 9 wherein step (a) comprises incubating for 30–40 minutes and the dissociation mixture comprises:
  0.5M NaCl,
  2–20 mM DTT,
  0.01–0.03% Polysorbate 80,
  0.5–5 mM EDTA,
  5–100 mM TRIS buffer, and
  0–50 mM phosphate at pH 8.2.

13. A method according to claim 9 wherein the dissociation mixture of step (b) comprises:
  at least 1M NaCl,
  0.01–0.03% polysorbate 80, and
  10 mM phosphate, pH 7.0.

14. A method according to claim 9 wherein the reassembly buffer of step (c) comprises:
  1.0–1.35M NaCl,
  2 mM Ca+2,
  a pH 6.2 buffer selected from the group consisting of: 50 mM sodium citrate, 50 mM glycine and phosphate, and 50 mM citrate and phosphate.

15. A method according to claim 9 wherein the final buffer of step (d) comprises;
  0.5M NaCl and 10 mM histidine, pH 6.2.

16. A vaccine made by the method of claim 1.

17. A vaccine made by the method of claim 9.

* * * * *